United States Patent
Kemme et al.

[11] Patent Number: 6,126,608
[45] Date of Patent: Oct. 3, 2000

[54] PORTABLE ULTRASOUND DIAGNOSTIC SYSTEM WITH HANDSFREE DISPLAY

[75] Inventors: Frank Sixtus Jacobus Marie Kemme, Sittard; Johannes Hubertus Martha Willems, Maastricht, both of Netherlands

[73] Assignee: Pie Medical Equipment B.V., Maastricht, Netherlands

[21] Appl. No.: 09/314,039

[22] Filed: May 18, 1999

[51] Int. Cl.[7] ........................................................ A01B 8/00
[52] U.S. Cl. ............................................................ 600/459
[58] Field of Search ................................... 600/437, 443, 600/447, 459; 73/625–626; 367/7

[56] References Cited

U.S. PATENT DOCUMENTS

| | | | |
|---|---|---|---|
| 5,293,351 | 3/1994 | Noponem | 367/7 |
| 5,295,485 | 3/1994 | Shinomura et al. | 128/660.07 |
| 5,590,658 | 1/1997 | Chiang et al. | 128/661.01 |
| 5,617,864 | 4/1997 | Stouffer et al. | 600/459 |
| 5,690,114 | 11/1997 | Chiang et al. | 128/661.01 |
| 5,722,412 | 3/1998 | Pflugrath et al. | 128/662.03 |
| 5,738,099 | 4/1998 | Chang | 128/662.03 |
| 5,817,024 | 10/1998 | Ogle et al. | 600/447 |
| 5,938,096 | 8/1999 | Sawer et al. | 224/625 |
| 5,964,709 | 10/1999 | Chiang et al. | 600/447 |
| 5,982,520 | 11/1999 | Weiser et al. | 359/172 |
| 6,015,091 | 1/2000 | Rochstein et al. | 235/472.1 |

OTHER PUBLICATIONS

Minivisor Service Manual from Organon Teknika (Sep. 1979).

Ultra PCI Systems Specifications from Advanced Medical Products of Columbia, SC (date unknown).

"Market for portable ultrasound could top $500 million in five years," Diagnostic Ultrasound Industry Report, Jun. 1998, pp. 1, 16–20.

*Primary Examiner*—Francis J. Jaworski
*Attorney, Agent, or Firm*—Baker & Daniels

[57] ABSTRACT

An ultrasound diagnostic system with a display wearable by a user such that the display does not fully occupy a user's hand during system operation. In one embodiment, the display is provided in a main unit that is shaped to fit on top of the forearm of the system user. An attachment mechanism of the main unit encircles the forearm. The main unit mounted on the arm receives data from a handheld scanhead used to obtain the ultrasonic images. In an alternate embodiment, the main unit may be operatively connected to a strap that loops around the neck of a user to allow the display to be suspended in front of the system user. Peripherals, such as a keyboard and a printer, may be operatively connected to the main unit by way of a wireless interface, such as an infrared connection.

19 Claims, 8 Drawing Sheets

PORTABLE ULTRASOUND DIAGNOSTIC SYSTEM WITH HANDSFREE DISPLAY

BACKGROUND OF THE INVENTION

The present invention pertains to ultrasonic diagnostic systems, and, in particular, to a portable ultrasound diagnostic instrument which may be readily transported on site or between sites.

Conventional ultrasound imaging systems are large, bulky instruments. Such systems typically comprise a transducer connected by a cable to a large, rack mounted unit that contains the processing and display components. The customary focus of such existing systems is to provide sophisticated signal processing and computing power to achieve the highest possible image quality. However, these large and complex types of systems are not sufficiently portable for convenient use in many applications, and further not all potential uses of ultrasound technology require all of the features with which these systems have been equipped, often at significant increased cost.

As a result of advances in the underlying technology which have permitted miniaturization of necessary electronics, the ultrasound industry continues to reduce the size and weight of available diagnostic equipment. The smaller and lighter equipment has improved portability such that in many cases the ultrasound equipment can be easily brought to the patient for diagnostic purposes instead of the patient being required to come to the ultrasound equipment. However, and while perhaps useful, existing portable ultrasound technology is not without its limitations.

One shortcoming of some portable systems is that the need to hold onto or otherwise manipulate the equipment with both hands during use hinders the ability of a person to productively use the system in some situations. For example, a system shown in U.S. Pat. No. 5,590,658 includes a lap top computer with the capability of displaying ultrasound images obtained with a handheld scan head. In practice, in order to ensure the display is visible at all times during the obtaining of the ultrasound images with the scan head, the user must either hold the lap top computer, or rearrange the computer on the surface on which it sits to face the user who may be moving around to position the scan head in a suitable location. A user may be forced to move about repeatedly in some situations, such as during veterinary ultrasound examinations when a larger animal or a reluctant animal is being examined. As a result, the system user's hand not being used to manipulate the scan head is often nonetheless occupied and not always free to assist with the medical procedure.

Other portable ultrasound systems, such as disclosed in U.S. Pat. Nos. 5,722,412 and 5,738,099, integrate the display and the transducer in the same unit. While in essence permitting the scan head and the display to be held in one hand, these systems suffer from a different shortcoming. In particular, in order for the ultrasound user to get the desired view, it is frequently necessary to move the transducer repeatedly to different regions of the patient and to different orientations. In so doing, the displays of these systems may not be sufficiently visible to a user unless that user moves about, possibly into awkward positions.

Thus, it would be desirable to provide a portable ultrasound system which overcomes these and other shortcomings of the prior art.

SUMMARY OF THE INVENTION

The present invention provides an ultrasonic diagnostic system with a handsfree display. The portable main unit in which the display is located may be attached to and worn by the user, such as on her arm, to allow its operation without occupying a hand at all times. The electronics are selected to achieve a low-cost system with a sufficient image quality for certain applications, thereby better enabling a range of applications including battlefield operations, veterinary medicine, emergency medicine, and advanced diagnosis during common doctor house calls. To maintain low weight of the main unit, peripherals such as a full keyboard and a printer are not incorporated into the main unit and may be circuited with the main unit via a wireless interface.

In one form thereof, the present invention provides a portable ultrasound system including a scanner for transmitting to and receiving from a region of interest an ultrasonic signal, circuitry in communication with the scanner for forming an image of the region of interest based on the ultrasonic signal, and a display for displaying the formed image which is furnished in a module wearable by a system user.

In another form thereof, the present invention provides a portable ultrasound system including a handheld scanhead with means for transmitting at least one ultrasonic signal into a region of interest and receiving the at least one ultrasonic signal reflected from the region of interest, a main unit operably connected to the handheld scanhead and including a display for displaying an image, means for attaching the main unit to a system user in a handsfree arrangement in which the display is visible to the system user during use, whereby the main unit during use need not continuously occupy a hand of the system user, and means, installed within at least one of the handheld scanhead and the main unit, for converting data from the transmitting and receiving means into an image of the region of interest which is then displayed on the display.

One advantage of the ultrasound diagnostic system of the present invention is that the display may be worn by the user such that both user hands are not necessarily occupied during use of the system.

Another advantage of the ultrasound diagnostic system of the present invention is that it is readily portable to allow it to be conveniently carried to and used with a patient, thereby enabling use in varied locations, including battlefield environments, such as for abdominal examinations in field emergency and trauma work, veterinary medicine environments and emergency medicine environments, such as for a vital systems check along the lines of internal bleeding, ruptures and the like.

Another advantage of the portable ultrasound diagnostic system of the present invention is that relatively simple measurements, such as distance, fetal age and residual bladder volume, which now may require an expensive scanning session in a hospital, may be performed more economically during a house visit by a doctor.

Still another advantage of the portable ultrasound diagnostic system of the present invention is that by leaving one hand unencumbered, it facilitates medical procedures such as biopsies and detection of kidney and bladder stones.

Yet another advantage of the portable ultrasound diagnostic system of the present invention is that it may be produced at a relatively low cost, thereby enabling certain applications, such as leaving an ultrasound scanner with suitable image quality for the application inside an infectious hazardous area.

Another advantage of the portable ultrasound diagnostic system of the present invention is that different versions may be manufactured which each have capabilities customized for a particular task, such as pregnancy detection in veterinary medicine, thereby improving efficiencies of use.

Still another advantage of the portable ultrasound diagnostic system of the present invention is that it is may be designed for use in rough environments, as well as for easy cleaning for hygienic purposes.

BRIEF DESCRIPTION OF THE DRAWINGS

The above mentioned and other advantages and objects of this invention, and the manner of attaining them, will become more apparent and the invention itself will be better understood by reference to the following description of embodiments of the invention taken in conjunction with the accompanying drawings, wherein.

Figure 1:
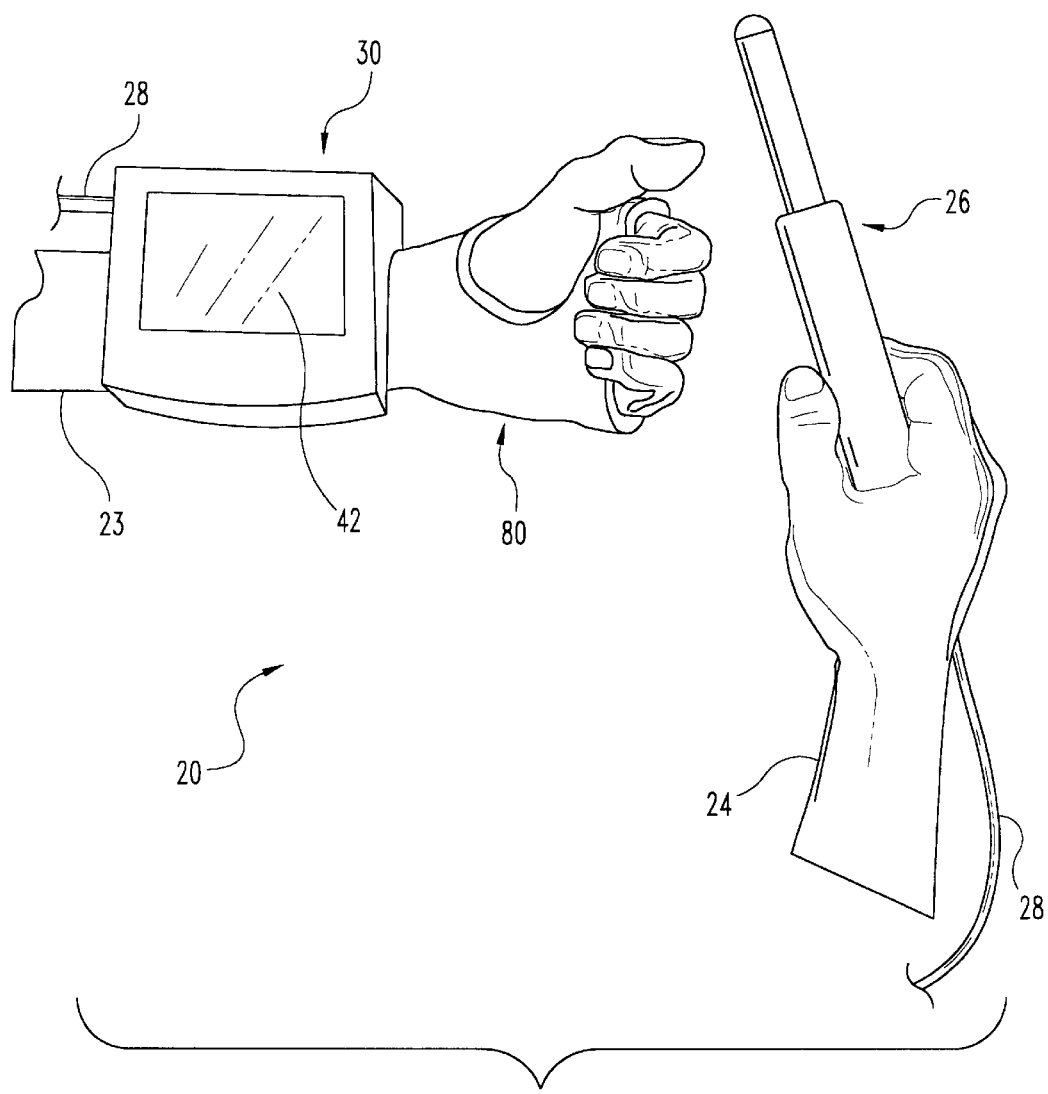
FIG. 1 is a diagrammatic perspective view of a first embodiment of a portable ultrasound diagnostic apparatus according to the present invention shown being worn by a user.

Corresponding reference characters indicate corresponding parts throughout the several views. Although the drawings represent embodiments of the present invention, the drawings are not necessarily to scale and certain features may be exaggerated or omitted in order to better illustrate and explain the present invention.

DESCRIPTION OF THE PREFERRED EMBODIMENTS

Referring now to the perspective view of FIG. 1, there is shown a first embodiment of a portable ultrasound diagnostic system with handsfree display configured according to the present invention. The ultrasound system, generally designated 20, is shown being used by a single person or system user, the left and right forearms of whom are indicated at 23 and 24, respectively. In this illustrated embodiment, ultrasound system 20 includes a handheld scanhead 26 that is electrically connected via cable 28 to an ergonomically designed main unit 30 releasably fastened to and worn on forearm 23. The shown positioning on the left arm, and the fact that the left hand is free to, for example, hold an animal during an ultrasound procedure, results in ultrasound system 20 being of particular use in veterinary obstetrical applications, such as pregnancy detection and fetal viability, as well as gynecological studies, such as follicular development and uterine pathology, of pigs, other animals of comparable size and large animals such as mares and cows. Naturally, with a different attachment member or with the same attachment member if symmetrical so as to allow use on both the left arm and right arm as described below, system 20 may be adapted for use by a person who wishes to mount the main unit on her right arm and manipulate scanhead 26 with her left hand.

With additional reference to FIGS. 2–5, main unit 30 includes a protective housing 32 assembled from a pair of mating, front and back parts made of a durable but lightweight material, such as plastic. To reduce electro magnetic interference (EMI) and to better ensure that federal electro magnetic compatibility (EMC) regulations are met, a conductive coating is provided on the inside surfaces of housing 32. A preferred coating is a sputtered conductive coating consisting of a four micron thick sandwich construction of a layer of stainless steel, which is provided to avoid deterioration of the plastic housing, a layer of copper for shielding, and finally a covering layer of stainless steel. This conductive coating can reach damping of approximately 75 dB. Housing 32 has overall width and height dimensions each of approximately fifteen centimeters. Housing 32 includes a depth dimension, as measured independent of the cable inlet, generally designated 35, to which cable 28 is permanently attached, of approximately eleven centimeters. While larger or smaller sized housings may be employed within the scope of the present invention, this housing size provides adequate capacity for the enclosed hardware while not resulting in an overly bulky or awkward attachment.

Cable 28, fed through cable inlet 35, is connected to the system's internal electronics and protrudes rearward through a rectangular opening 38 in the back wall of housing 32. Cable inlet 35 is EMC shielded and is constructed to provide a permanent cable attachment that reduces the likelihood of sensitive coaxial cables internal to cable 28 breaking when the cable is subject to pull forces. Two series of plate holes 39 and plate openings 41, positioned over a fan internally mounted in housing 32, are provided in a plate connected to the internal frame and are exposed by housing opening 38 to allow air to be circulated by the internal fan to cool the system components. Also positioned on the back of the housing is power connector 37 into which the external power supply is plugged, and a not shown video connector proximate connector 37, which allows connection with a larger monitor to display the image.

A planar front surface 38 of housing 32 includes a rectangular aperture 40 that is covered by a thin piece of plexiglass and through which is visible a flat display viewscreen 42, such as a TFT-LCD, on which the images acquired through use of system 20 are displayed.

Keypads of a keyboard on main unit 30 are circuited with the electronics enclosed within housing 32 and allow a system user to interface with the computer software of the ultrasound system to achieve the desired system functionality. Keypads using foil keyboard technology known to those of skill in the art are preferred to keep cleaning relatively easy. A foil keyboard is directly adhered to planar front surface 38 of the plastic housing, and electrical connections of the keyboard to the internal electronics are fed through a small slit provided in the housing. The foil keyboard is provided with a transparent window over the LCD screen 42. This transparent window preferably has been roughened to avoid the appearance of Newton rings if the keyboard window is pressed against the plexiglass covering the display. Keypad 44 of the keyboard is used to turn main unit 30 on and off. In the shown embodiment, cursor control keypads 45, 46, 47 and 48 are depressable to move a cursor displayable on the LCD screen 42 in up, down, left and right directions, respectively, such as for measurement over the screen. Cursor movements in conjunction with other keys of the control keypad enable a user to navigate system options listed on displayed menu pages. For example, set button 49 is used in combination with cursor keys 45–48 to step through the on-screen menus. When set button 49 is pressed, the cursor keys are provided with their second functions, namely up, down, escape and select, and the on-screen menus appear. Up keypad 45 and down keypad 46 may be used to move a cursor upward or downward in the menu. Select keypad 48 is used to select a function or enter a deeper level in the menu structure, and escape keypad 47 is used to leave a certain deeper level to return to a previous menu level. The various menus are preferably designed not to open automatically, but rather only to be opened explicitly to avoid cluttering the small display with too many menus. The menus are also stacked on top of each other when displayed in order to save display space. Keypad 51 is a user-programmable function key, or macro key, which allows a system user to program a desired, regularly used function to that key. Keypad 51 also may be designed in some versions to provide a second function which is activated only when the system programming runs a particular application or displays a certain menu. Keypad 52 is used to adjust the field of view of the system. Plus key 54 and minus key 55 adjust the brightness of the displayed image. Freeze keys 57 and 58 are depressable to hold the image displayed on LCD screen 42.

Figure 2:
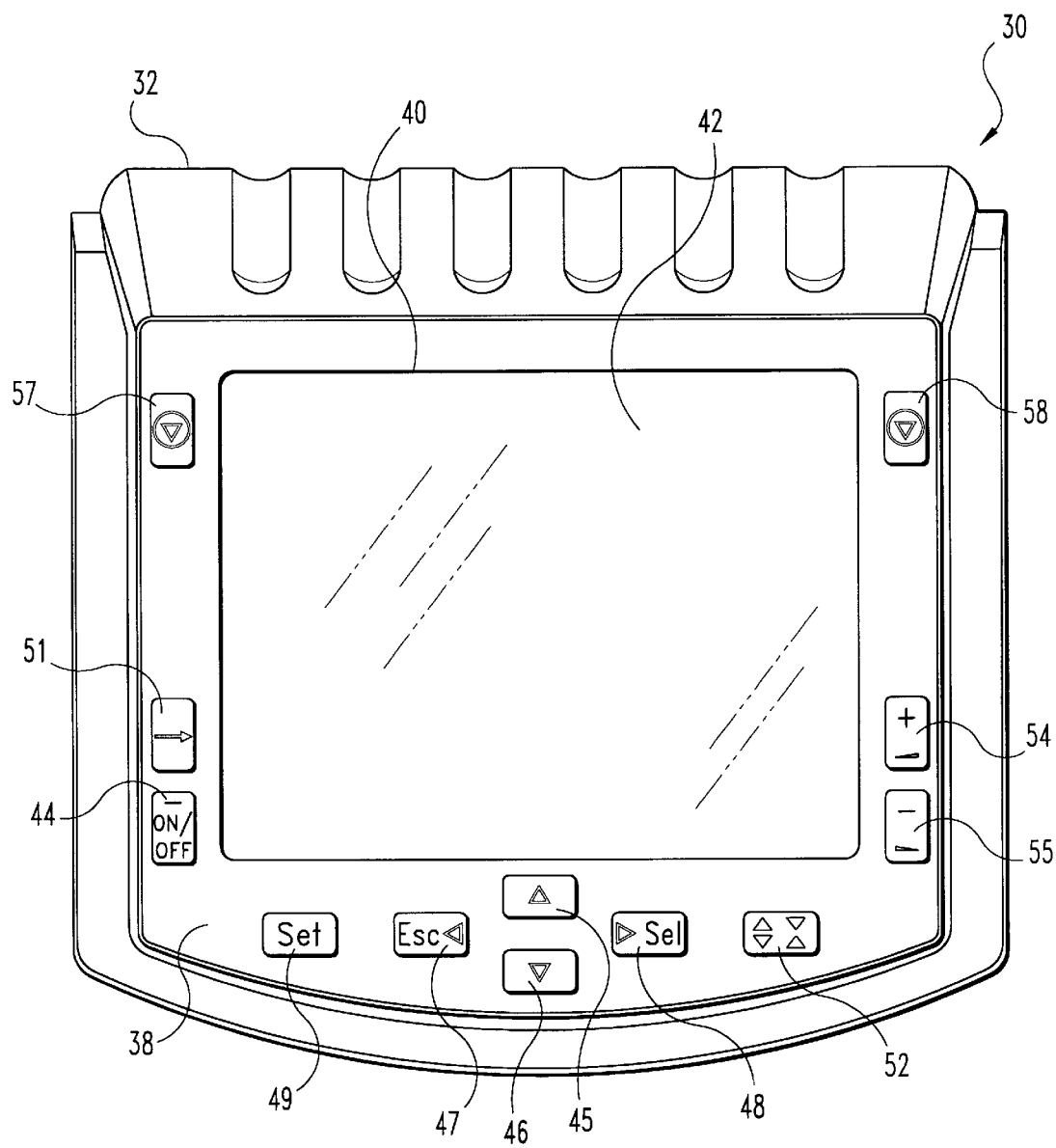
FIG. 2 is a front elevational view of the arm-mounted main unit of the apparatus of FIG. 1 shown removed from the user and separate from the remainder of the apparatus.
Figure 3:
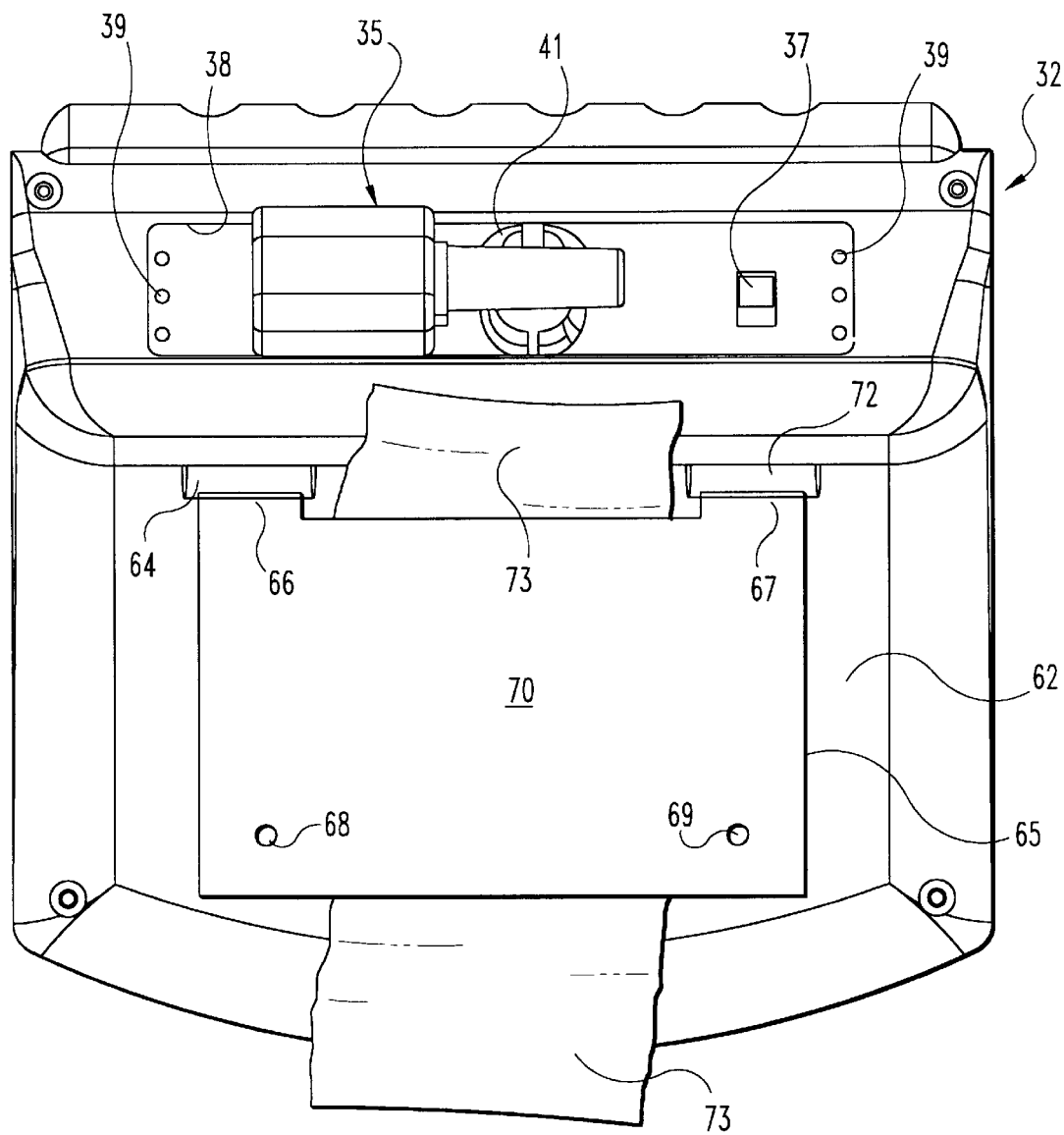
FIG. 3 is a rear elevational view of the arm-mounted main unit of FIG. 2.

Arrangements of the keypads which are different than the arrangement shown in FIG. 2 alternatively may be employed within the scope of the present invention. In addition, specialized keypads in addition to keypad 51 which control operations of the system only accessed through the menus in system 20 may be employed in alternate ultrasound system versions, such as in versions that only include more limited features in order to increase efficiencies in specific applications that merely require those features.

Figure 4:
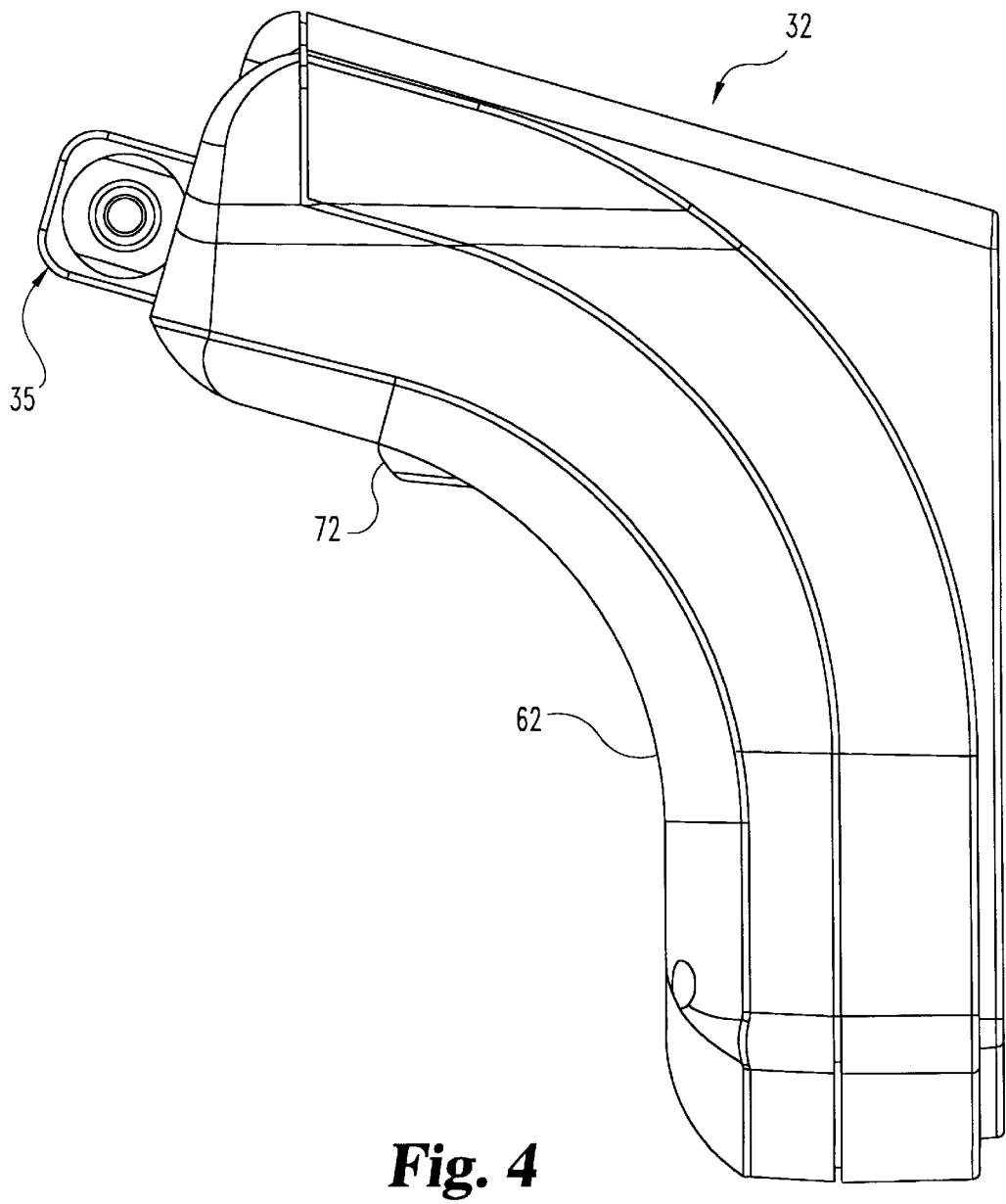
FIG. 4 is a left side elevational view of the arm-mounted main unit of FIG. 2, wherein the fastener adaptor shown in FIG. 3 is removed for purposes of illustration.

The rear surface 62 of housing 32 is concavely designed to fit comfortably around the top of forearm 23 of the user. As best shown in FIG. 4, the concavity of rear surface 62 is furnished in a smoothly curved shape with a radius of curvature of approximately fifty centimeters. Others curvatures, including those within the range of thirty to sixty-five centimeters, as well as forearm-accommodating concavities formed in different shapes, may alternatively be employed within the scope of the present invention.

Tab-accommodating slots are provided in the base of projections 64 and 72 integrally formed with rear surface 62. A fastener element, utilized to connect main unit 30 to the forearm in the preferred embodiment, comprises a bracket 65 that is detachably mounted to the housing 32. Bracket 65 includes upwardly extending tabs 66 and 67 that fit within the slots provided in projections 64 and 72. Bracket 65 is made of a thin aluminum plate, or another sufficiently durable and rigid material, and is concavely shaped to conform to the housing rear surface 62. Screws 68 and 69, received within tapped bores provided in the housing, complete the securement of fastener element bracket 65 to the housing. The outward or rearward facing surface 70 of bracket 65 is provided with a Velcro-type fastener component, preferably over its entire area. A wide, flexible belt 73 is attached to fastener bracket 65 in any suitable known fashion and has sufficient length to be wrappable around the forearm of a user. Belt 73 may be attached to main unit 30 merely by being sandwiched between housing 32 and bracket 65. Belt 73 is provided with not shown fasteners, such as mating Velcro components, on its opposite ends to allow the ends to be fastened together in adjustable encircling belt lengths. Belt 73 provides a back-up attachment system to the forearm in case the fastener on bracket surface 70 becomes disengaged from the mating Velcro fastener component provided on a wearable, forearm encircling wrap. Differently configured back-up attachment systems, including multiple belts, may alternatively be employed.

When fastener bracket 65 is removed, the slots in projections 64 and 72 can be used to mount main unit 30 to a pedestal or stand, placeable on a support surface, when main unit 30 is to be used in a stand-alone mode.

Figure 5:
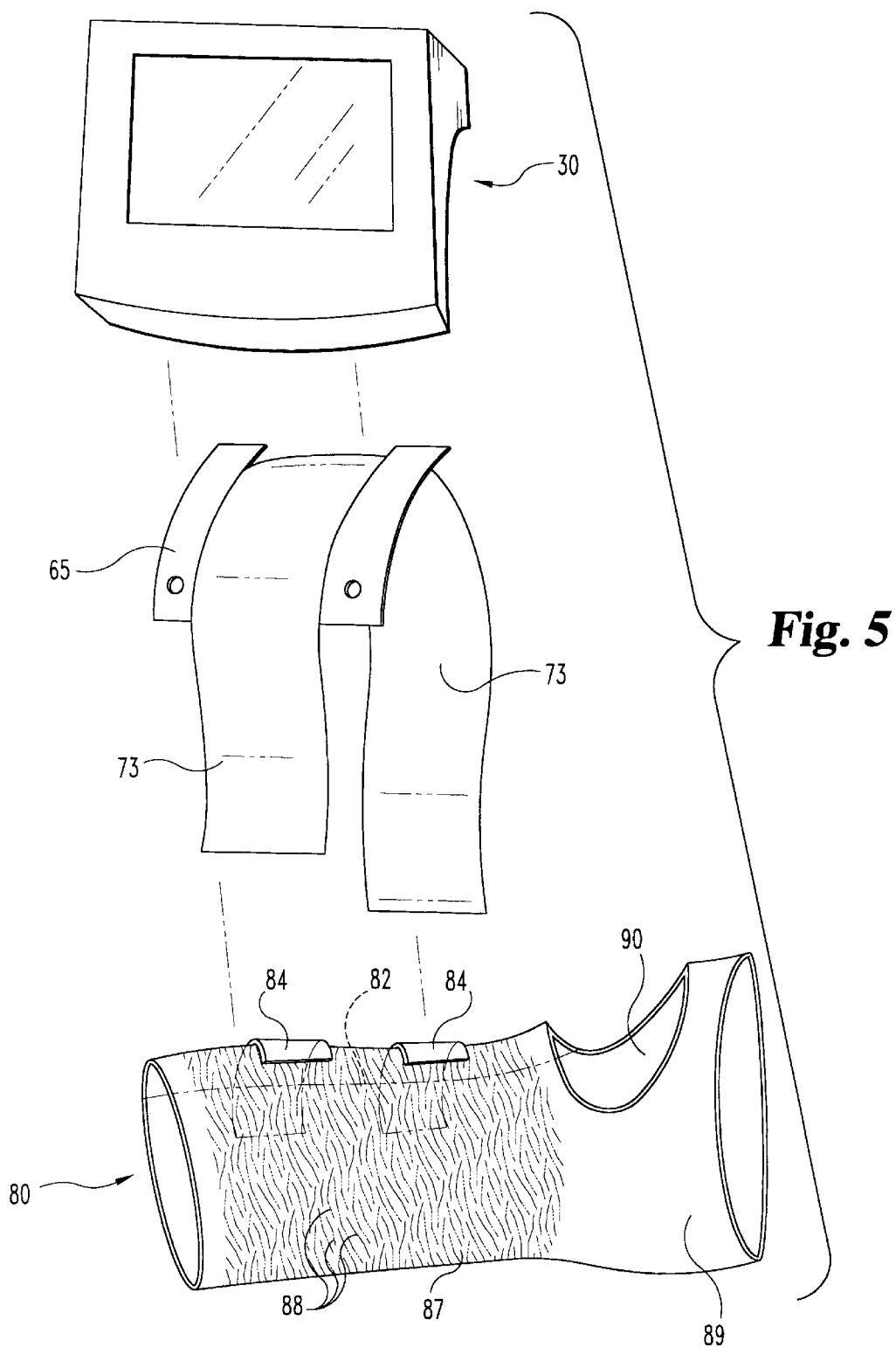
FIG. 5 is a diagrammatic, exploded front perspective view of the main unit and the sleeve-type attachment member used to mount the main unit to the user's forearm.

With additional reference to the diagrammatic view of FIG. 5, the attachment member, generally designated 80, is shown unfastened from the main unit 30. Attachment member 80 allows a user to maintain the display in a usable position without the use of either hand. Attachment member 80 is made of a flexible fabric and has a slit 82 running along its length which facilitates it being put on by a user. Multiple straps 84 allow attachment member 80 to be adjustably fastened tightly around the forearm once slipped on by a user. Straps 84 are shown only partially circumscribing the member 80 for purposes of illustration, but in alternate embodiments may be of different lengths, including lengths that allow the straps to be wrapped all the way around member 80. A single strap may also be used. Straps 84 are provided with fasteners, such as Velcro, to allow their adjustable securement to member 80, provided suitable complementary fasteners are provided thereon, or to other parts of the straps in situations where the straps wind completely around the attachment member 30. In alternate embodiments, rather than a slitted member, attachment member 80 may be provided as an elastic, tubular sleeve which tightly fits over the arm.

Around its entire circumference and along its length, a wrist-covering region 87 of attachment member 80 is provided with Velcro fastening components, indicated generally at 88, of the type complementary or mateable to the Velcro components provided at 70 on fastener bracket 65. This complete coverage allows main unit 30 to be placed on virtually every desirable position of the attachment member 80, both with respect to the location along the length of the forearm as well as the rotational orientation of the main unit 30 on the arm. While other known complementary fasteners may be provided on member 80 and the fastener bracket 65, Velcro components are the preferred fastener due to the fact that a great variability in the mounting of the main unit is obtained. Lower palm-covering portion 89 extending forward from region 87 includes an opening, such as aperture 90 shown, through which the thumb of the user projects when worn. Attachment members that fit over more or different digits of the hand than the shown thumb digit, or that merely fit over the wrist, may alternatively be employed.

Although shown as having a configuration more suitable for use on the left arm of a system user, the attachment members may be alternately configured, such as an attachment member with a more symmetrical configuration that is suitable to be worn on either the left arm or the right arm of users, to accommodate both left-handed and right-handed users of the ultrasound system of the present invention.

In an alternate embodiment not shown, rather than using a fastener bracket 65 which is attachable to the complementarily designed attachment member 80 to mount the main unit, one or more adjustable, fastenable straps that are attached to the main unit housing via one or more belt-accommodating loops provided therein may be tightly secured around the forearm to attach the main unit to the forearm. However, only using one or more straps to mount the main unit on the person is less preferred due to the fact that a greater chance of the unit rotating around the arm during wearing results.

Figure 6:
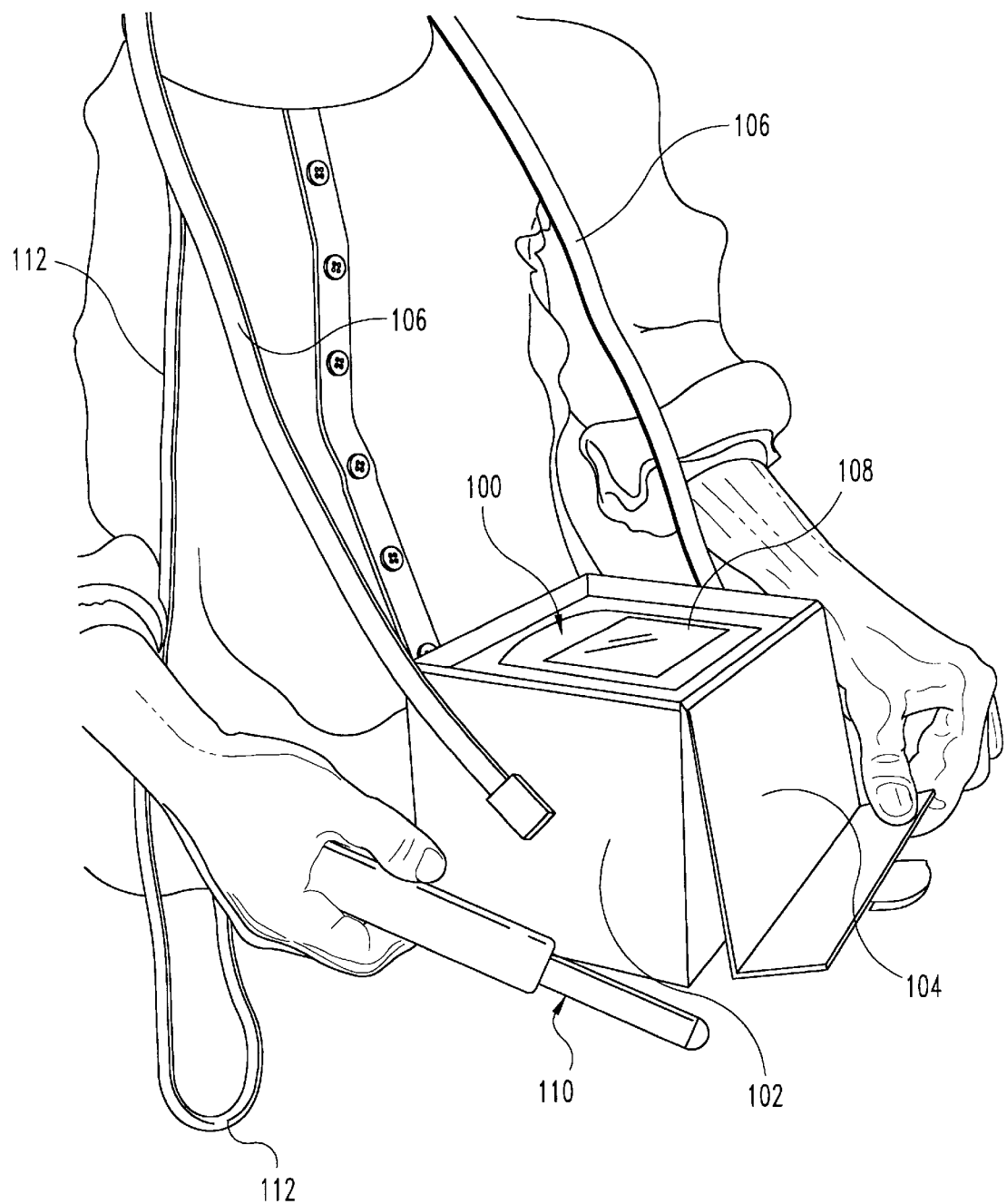
FIG. 6 is a diagrammatic perspective view of a second embodiment of a portable ultrasound diagnostic apparatus according to the present invention shown being worn by a user.

Referring now to FIG. 6, there is diagrammatically shown in use a second configuration of the present invention that enables a handsfree wearing of the system display by the user. In this embodiment, which is particularly well suited for use during obstetrical and gynecological studies of mares and cows, system main unit 100 is installed in a parallelepiped-shaped box or container 102. A hinged lid 104 is designed to be folded back over the top opening of container 102 and fastened to container 102 to protectively cover main unit 100 when not in use.

A strap 106 having opposite ends attached to the sides of container 102 is adapted for looping around the user's neck. The length of strap 106 is preferably adjustable to allow container 102 to be suspended at a comfortable height for each user, such as a height generally corresponding to that user's abdomen at which the display may be readily focused on but without being bumped by the legs during walking.

The interior compartment of container 102 is customized to main unit 100 such that display 108 of main unit essentially faces directly upward and is at a height proximate the container top edge. This interior compartment customization can be of various forms such that main unit 100 may be shaped similarly to main unit 30, or to display units differently configured. While an LCD screen with a large viewing angle is preferably selected, the shown orientation of display 108 permits a LCD screen with even a limited viewing angle to be employed in main unit 100.

A handheld scanhead 110 may be used by either the right hand or left hand of the user. Scanhead 110 is electrically connected via cable 112, the not shown opposite end of which passes through a not shown access opening in the side of container 100 and is connected to a plug provided on main unit 100. Cable 112 is preferably of such a length to allow a user to drape cable 112 up and around the neck to make scanhead 110 easier to carry.

Figure 7:
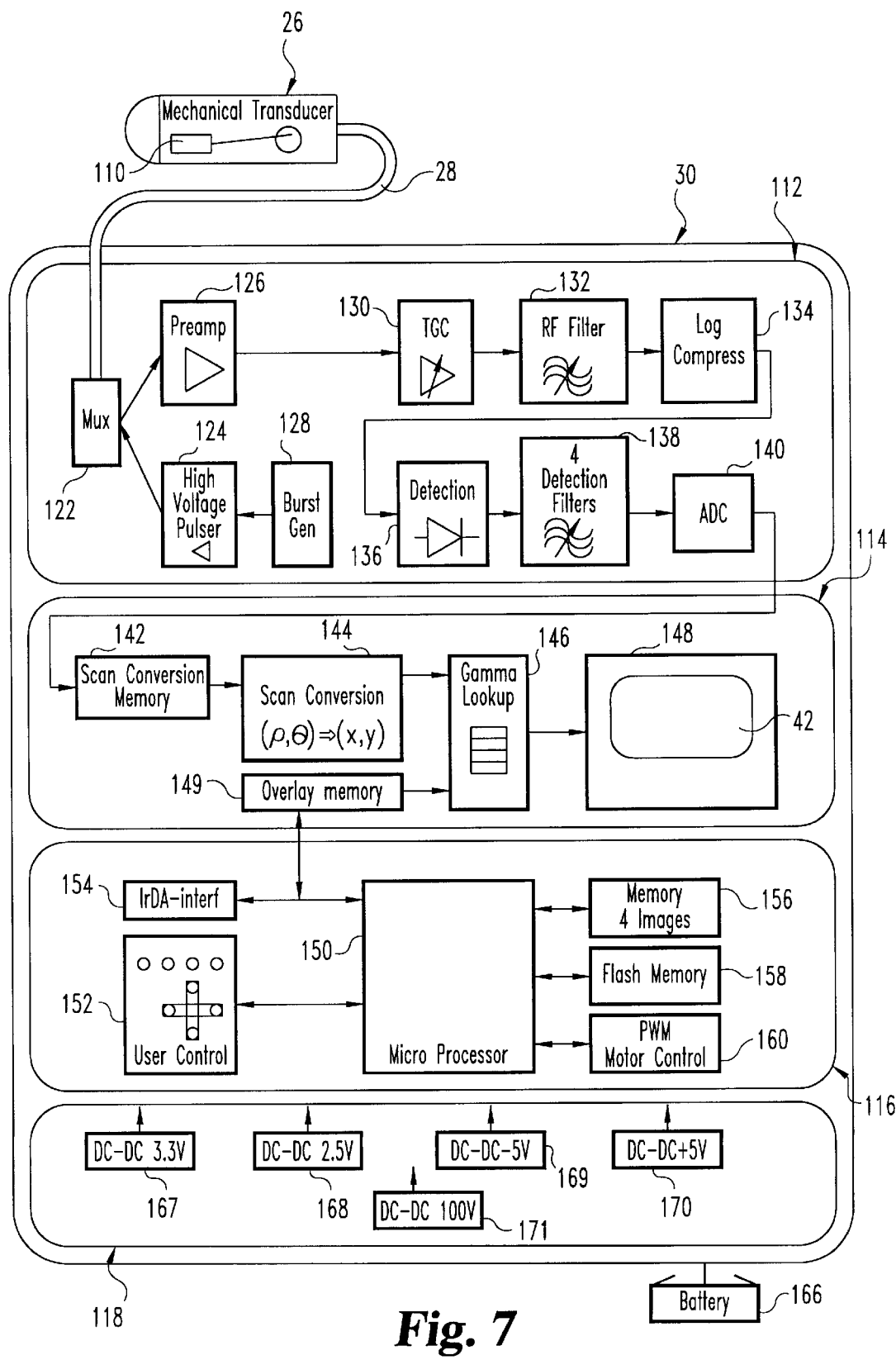
FIG. 7 is a block diagram illustrating the internal architecture of an apparatus of FIG. 1 which utilizes a mechanical sector scanner and an analog front-end.

With reference now to FIG. 7, which schematically shows one suitable configuration, the internal electronic circuitry of ultrasound system 20 will be described. The circuitry shown in FIG. 7 is merely illustrative, and not intended to be limiting, and further the basic operations of this shown type of circuitry are generally well known and therefore not exhaustively described herein. The shown circuitry, which achieves a relatively low cost and low weight for the system, is not necessary to practice the present invention as the handsfree display of the present invention may find advantageous use with a variety of alternate electrical circuitries that may be implemented by those of ordinary skill in the art.

Scanhead 26 is equipped with a single element mechanical sector transducer 110 that transmits ultrasonic signals into a region of interest, such as human or animal tissue, and receives the returning ultrasound echos reflecting back from this tissue. Transducer 110 comprises a single piezoelectric element and a controlling motor that are mounted in scanhead 26. The piezoelectric element functions to scan a sector from the desired field of view. A stepper motor is preferred for the motor of transducer 110, but other motors such as a linear electrical motor, may also be employed. A pulse width modulation motor control 160 within main unit 30 optimizes the current dissipation in the stepper motor of transducer 110, and to further reduce the dissipation, the motor current is automatically switched off temporarily if the step rate of the motor falls below a programmed minimum value. Different transducers, such as an electronic linear transducer or a convex array transducer, may naturally be substituted for the shown transducer within the scope of the present invention. Still other suitable transducers include a mechanical MAP probe appropriate for fertility diagnosis, and a mechanical translational linear probe which mimics with just one channel a electronic linear probe.

Transducer 110 communicates received data to main unit 30 via coaxial cable 28. In an alternate embodiment with circuitry modifications, a wireless interfacing of the data between scanhead 110 and main unit 30 may be provided such that cable 28 is eliminated. In the shown embodiment, main unit 30 contains all the electronics necessary to create a diagnostic ultrasound instrument and generally comprises a single channel analog front-end 112 that amplifies and processes the transducer signal, a highly integrated digital back-end 114 in a field programmable gate array that formats and displays the processed signal, a control system 116, and a power supply 118. In a preferred embodiment, the electronics of main unit 30 are compressed onto a single circuit board that is stacked between ground layers within housing 32 to aid in preventing EMC. To keep the weight of the main unit low, no metal shielding of the circuitry is provided, but an aluminum frame is provided which carries the system components such as the circuit board, connectors, and display, and acts as the base to which the housing portions are screwed or otherwise fastened. The circuit board has an analog and digital section divided by a small piece of flexprint which allows the board to be bent to fit into housing 32. As alluded to above, different circuitry may alternatively be employed, such as circuitry with a highly integrated multi-channel digital front-end for use with a linear transducer or one in which components now present in main unit 30, such as the preamplifier, were incorporated into scanhead 26.

Cable 28 is connected to a multiplexer 122 of front-end 112 which selectively provides transducer 110 with a connection to both a high voltage driver circuit 124 and a sensitive reception circuit or preamplifier 126. High voltage driver circuit 124 is driven by a burst generator 128 that makes possible the generation of single period RF signals necessary to achieve an as high as possible signal bandwidth for the transmitted ultrasound pulses. High bandwidth, very short pulses are necessary to ensure maximum axial resolution in echo mode, which is also known as B-mode.

The electrical signal converted from the received ultrasound echo by the piezoelectric element of transducer 110 is first amplified by a low noise preamplifier 126 and then fed to a time-varying gain control, or TGC, circuit 130. Low noise preamplifier 126 largely optimizes the overall noise behavior in the reception path, and TGC circuit 130 compensates for the exponential attenuation of the sound pulse as it travels through human or animal tissue. Preamplifier 126 uses a voltage clamping circuit that prevents it from overloading in receive mode.

The signal from preamplifier 126 is filtered by RF filter 132 that selects the desired band of interest. The amplified electrical signal is then forwarded to analog logarithmic compressor 134 in which the desired dynamic range of the received echo signal, typically 65 dB, is compressed to the available dynamic range of the display unit, typically 40 dB. The compressed signal is then fed to detection circuit 136, which detects the envelope of the RF signal by rectifying and averaging the signal. The rectified signal is then filtered by a detection filter that can be selected out of a bank of four possible detection filters 138 to match the signal bandwidth to the available video bandwidth given by the number of video lines that can be displayed on the display unit.

The analog signal output from detection filter 138 is processed by analog-to-digital converter 140 that outputs a digital signal to digital back-end 114 which is stored in memory 142. The digitizing rate of converter 140 is matched against the number of video lines that can be displayed on display unit and the desired depth of view in order to match and thereby optimize the amount of data processed to the information content that can be made visible.

The digitized data from memory 142 is used by digital scan converter 144 that converts the digitized signal data from polar sector coordinates (r, θ) to rectangular video coordinates (x, y). After the scan conversion by converter 144, the rectangular video data is fed through post processing circuitry generally indicated at 146 that comprises a user selectable gray scale map and a gamma correction table to correct for the non-linear response of the display unit 148 comprising LCD screen 42. The user selectable gray scale map is optimized to highlight or clarify certain regions of interest within the gray range for certain applications. Overlay memory 149 is used to display text, on-screen menus, cursors and the like.

The control system 116 includes a digital control circuit, preferably a low power microprocessor 150, that controls the operation of ultrasound system 20. As is known in the art, microprocessor 150 controls the various signals that are necessary for proper operation of the system, such as the time gain control. Microprocessor 150 also interfaces with the user control keypads, indicated generally at 152, located on the front surface 38 of housing 32 to accept user settings and to make system adjustments based on user input as to features such as overall gain and contrast, the desired dynamic range, the desired gray map and the like. Microprocessor 150 is also circuited with interface electronics 154 that permits a wireless, such as infrared, communication by system 20 to external peripherals. These peripherals, which may take many forms such as a keyboard, printer, external image storage or a external computer, facilitate additional user input, output and connections. Therefore, while main unit 30 is functional for basic operation in a portable handsfree mode, the peripherals ensure that extra capabilities may still be performed to thereby allow basic operation of the device with main unit 30 as a standalone element that is not worn by the user. Microprocessor 150 also coordinates the storage of images on memory device 156, which is provided with battery backup.

The system software that controls microprocessor 150 is stored in flash memory 158 and is designed to permit the control of the system during portable use through the simple keypads provided on main unit 30. Software updates can be accomplished via infrared interfacing electronics 154 and are stored in flash memory 158. The system software is tailored by one of ordinary skill in the art to requirements of the specific operations for which system 20 in intended to be advantageously employed. For example, for systems to be economically employed during a house visit by a common house doctor, software that permits patient data entry, as well as measurements that are common practice, such as distance measurements, fetal age measurements and residual bladder volume measurements, may be provided.

The system software allows the storage of four images in internal memory 158, which makes possible the capture of images on site that can then be diagnosed off line. This image capturing capability better ensures a truly portable usage of system 20, as diagnosis or analysis is not forced on site.

Ultrasound system 20 is preferably powered by a battery, but a mains adapter connectable to a supply of alternating current is also within the scope of the invention. Power supply 118 is schematically shown in FIG. 7 as being attached to a battery 166 that feeds voltage to several switched DC—DC converters 167, 168, 169 and 170 of the power supply, which convert voltage to the operating voltages, namely 2.5 V, 3.3V, +5V, −5V, for the main unit components. Battery 166 also provides 100 V for high voltage driver circuit 124 through switched DC—DC converter 171. Switched DC—DC converters are used for maximum efficiency in the power conversion process, and to be able to optimize each voltage in the system so that it leads to a minimum of power dissipation.

Figure 8:
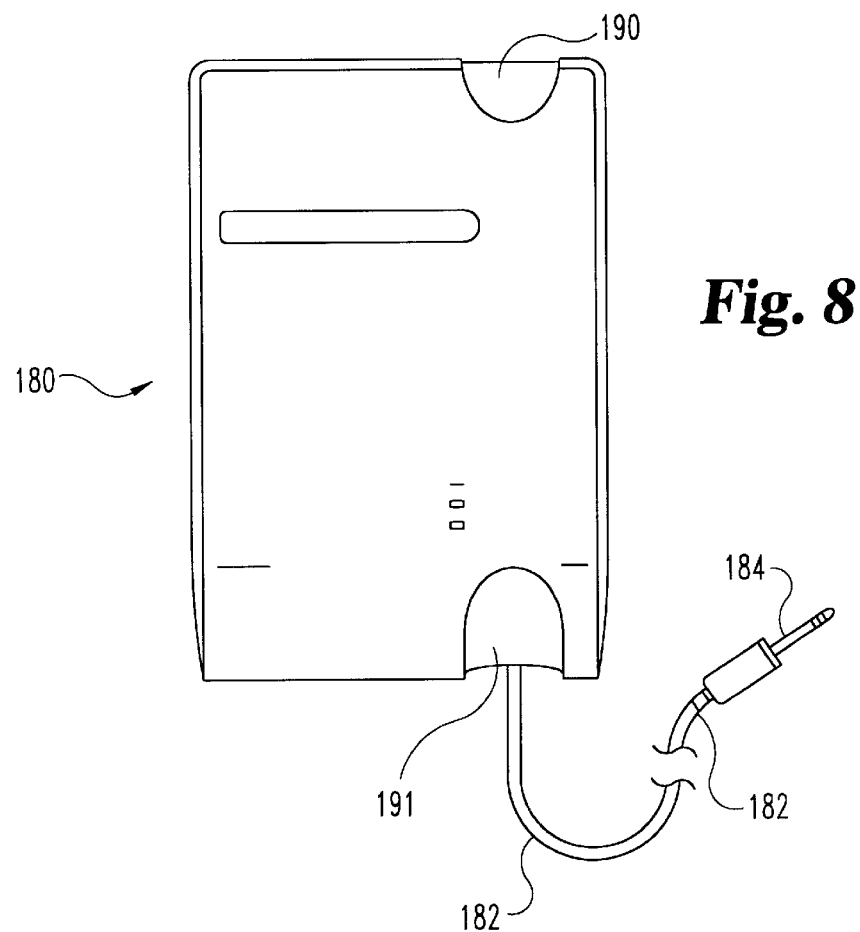
FIG. 8 is a front elevational view of a battery pack of which the connected battery cable is shown in an unwound configuration.
Figure 9:
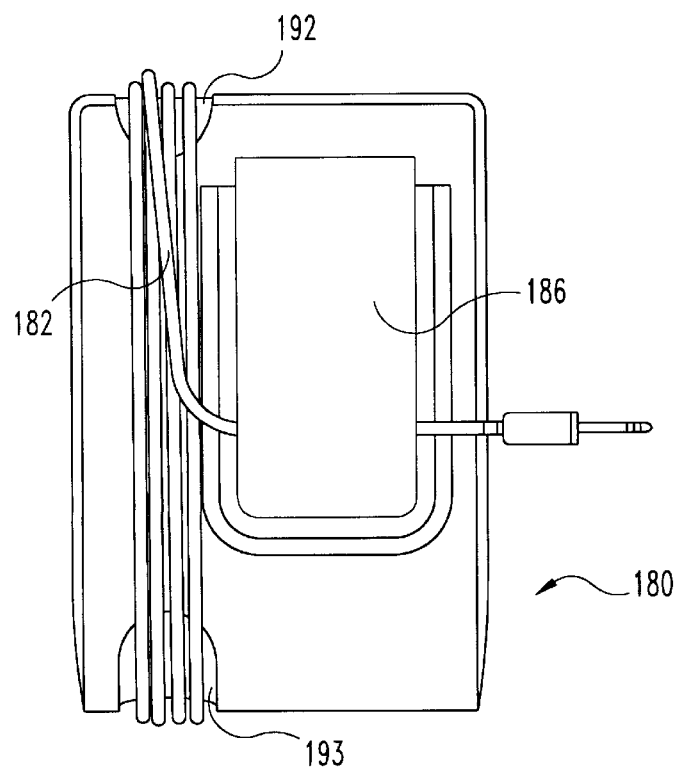
FIG. 9 is a rear elevational view of the battery pack of FIG. 8 after the battery cable has been wound around the housing for storage.

Battery 166 is typically located external to main unit 30. As shown in FIGS. 8 and 9, battery 166 may be provided in the form of a multiple NiMh batteries housed within a battery pack 180. Battery cable 182 extends from the housing of pack 180 as shown in FIG. 8 and includes a plug 184 attachable to a power connector of main unit 30. A clip 186 formed in the rear surface of the housing of battery pack 180 fits over a user's belt or waistband for easy carrying. Recessed or concave portions 190–193 formed in the front and rear surfaces of the housing of pack 180 keep cable 182 in place during storage after being wound when not in use as shown in FIG. 9. In an alternate embodiment, and more suitable when main unit 30 is to be used in a stand-alone mode, a battery pack can be attached to the rear of main unit 30 in place of fastener bracket 65 described above.

Features of the circuitry of FIG. 7 that have been selected to enable battery operation include low power color TFT LCD, pulse width modulation for the motor current, and 3.3 V and 2.5 V electronic components with local DC—DC converters for optimum power conversion. The illustrated circuitry achieves a power consumption of less than 20 W for system 20, which allows for approximately 3.5 hours of operation for a battery pack having at least 4500 mA/hr.

By selecting lightweight materials as well as utilizing technology as described above which is less complicated than that furnished in some other portable ultrasound devices, main unit 30 of ultrasound system 20 is kept very low weight. Specifically, and as long as battery 166 is mounted external thereto, main unit 30 can be provided with a weight of less than about 800 grams, more preferably of less than about 750 grams, and even more preferably about 733 grams.

While this invention has been shown and described as having multiple designs, the present invention may be further modified within the spirit and scope of this disclosure. For example, with further advances in technology enabling even greater miniaturization of the ultrasound electronics, the display could be incorporated into other wearable articles, such as a watch-type device. This application is therefore intended to cover any variations, uses, or adaptations of the invention using its general principles. Further, this application is intended to cover such departures from the present disclosure as come within known or customary practice in the art to which this invention pertains.

What is claimed is:

1. A portable ultrasound system comprising:
   a scanner for transmitting to and receiving from a region of interest an ultrasonic signal;

circuitry in communication with said scanner for forming an image of the region of interest based on the ultrasonic signal;

a display for displaying the formed image, said display being furnished in a main unit; and an attachment member for said main unit, said attachment member being mountable around a forearm of the system user such that said display is visible to the system user during use, said attachment member extending toward a hand of the system user at the end of the forearm and comprising a digit-accommodating opening.

2. The portable ultrasound system of claim 1 wherein said main unit comprises a housing including a forward facing surface on which said display is visible and a rearward facing surface, and wherein said rearward facing surface of said housing is concave shaped to fit on top of a forearm of the system user.

3. The portable ultrasound system of claim 2 wherein said main unit is releaseably secured to said attachment member with at least one fastener comprising mating hooks and loops.

4. The portable ultrasound system of claim 1 wherein said scanner comprises a handheld probe connected to said main unit by an electrical cable.

5. The portable ultrasound system of claim 4 wherein at least substantially all of said circuitry is disposed in said main unit.

6. The portable ultrasound system of claim 1 wherein said display comprises a flat screen display.

7. The portable ultrasound system of claim 1 wherein said main unit comprises a weight less than about 800 grams.

8. The portable ultrasound system of claim 1 wherein said attachment member comprises a portion structured to cover at least part of a palm of the system user, and wherein said digit-accommodating opening is located in said attachment member portion and arranged to provide a thumb-accommodating opening.

9. A portable ultrasound system comprising:

a handheld scanhead comprising means for transmitting at least one ultrasonic signal into a region of interest and receiving said at least one ultrasonic signal reflected from the region of interest;

a main unit operably connected to said handheld scanhead, said main unit comprising a display for displaying an image, said main unit comprising a housing with a forward facing surface on which said display is visible and a rearward facing surface, wherein said rearward facing surface is concave shaped to fit a forearm of a system user;

means for attaching said main unit to the forearm of the system user in a handsfree arrangement in which said display is visible to the system user during use, whereby said main unit during use need not continuously occupy a hand of the system user; and means, installed within at least one of said handheld scanhead and said main unit, for converting data from said transmitting and receiving means into an image of the region of interest which is then displayed on said display.

10. The portable ultrasound system of claim 9 wherein said attaching means comprises at least one belt operatively attached to said housing of said main unit and wrappable around the forearm of the system user when said housing is positioned on the forearm.

11. The portable ultrasound system of claim 9 wherein said attaching means comprises a member extending from said housing toward a hand of the system user at the end of the forearm, said member comprising a digit-accommodating opening.

12. The portable ultrasound system of claim 11 wherein said member comprises a sleeve in which fits the forearm of the system user, and wherein said member opening is structured and arranged to provide a thumb-accommodating opening.

13. The portable ultrasound system of claim 12 wherein said sleeve comprises a slit extending along at least a portion of a length of the sleeve to facilitate said sleeve being put on by the system user, and further comprising means for preventing said slit from opening during use.

14. The portable ultrasound system of claim 9 wherein said handheld scanhead is connected to said main unit by an electrical cable.

15. The portable ultrasound system of claim 9 further comprising means for wireless interfacing with at least one of a keyboard, a printer, and an external image storage system.

16. The portable ultrasound system of claim 9 wherein said system, exclusive of said scanhead, comprises a weight of less than about 800 grams.

17. The portable ultrasound system of claim 9 further comprising a battery pack circuited to said main unit, said battery pack comprising a belt clip for attachment to the system user.

18. The portable ultrasound system of claim 17 wherein said battery pack comprises a housing with concave portions about which a battery cable is wrappable for storage.

19. The portable ultrasound system of claim 9 comprising means for displaying menus of system functionality in said display, and keypad means for selecting functionality from said menus for system control.

* * * * *